United States Patent
Fabrega et al.

(10) Patent No.: US 8,211,662 B2
(45) Date of Patent: Jul. 3, 2012

(54) NITROREDUCTASE ENZYMATIC SUBSTRATES

(75) Inventors: Olivier Fabrega, Felines Minervois (FR); Arthur James, Cumbria (GB); Vindhya Lakshika Salwatura, Newcastle Upon Tyne (GB); Sylvain Orenga, Neuville sur Ain (FR); Stephen Stanforth, Northumberland (GB)

(73) Assignee: Biomerieux, Marcy l'Etoile (FR)

( * ) Notice: Subject to any disclaimer, the term of this patent is extended or adjusted under 35 U.S.C. 154(b) by 5 days.

(21) Appl. No.: 12/451,293

(22) PCT Filed: May 29, 2008

(86) PCT No.: PCT/FR2008/050935
§ 371 (c)(1),
(2), (4) Date: Apr. 5, 2010

(87) PCT Pub. No.: WO2008/152305
PCT Pub. Date: Dec. 18, 2008

(65) Prior Publication Data
US 2010/0221764 A1    Sep. 2, 2010

(30) Foreign Application Priority Data
May 31, 2007 (FR) .................................... 07 55373

(51) Int. Cl.
C12Q 1/26 (2006.01)
C07D 261/20 (2006.01)
C07D 263/52 (2006.01)
C07D 401/04 (2006.01)

(52) U.S. Cl. ......... 435/25; 546/198; 546/201; 548/217; 548/452

(58) Field of Classification Search .................... 435/25; 546/198, 201; 548/217, 452
See application file for complete search history.

(56) References Cited

U.S. PATENT DOCUMENTS

| 4,727,154 A | 2/1988 | Papenfuhs |
| 6,555,332 B2 | 4/2003 | James et al. |
| 2002/0031795 A1 | 3/2002 | James et al. |
| 2009/0142269 A1 | 6/2009 | Klunk et al. |

FOREIGN PATENT DOCUMENTS

| WO | WO 00/28073 | 5/2000 |
| WO | WO 2007/064773 A2 | 6/2007 |

OTHER PUBLICATIONS

Temiz et al., "Synthesis and microbiological activity of some novel 5- or 6-methyl-2-(2,4-disubstituted phenyl) benzoxazole derivatives," Il Farmaco, vol. 53, pp. 337-341, 1998.

Bougrin et al., "Trois Nouvelles Voies de Synthèse des Dérivés 1,3-Azoliques Sous Micro-ondes," Tetrahedron, vol. 54, pp. 8055-8064, 1998 (with Abstract).

Charris et al., "A convenient route to 2-substituted benzothiazole-6-carboxylic acids using nitrobenzene as oxidant," Journal of Chemical Research, pp. 769-770, Dec. 2006.

Chari et al., "Silica gel supported sodium hydrogensulfate as a heterogenous catalyst for high yield synthesis of 2-arylbenzothiazoles," J. Indian Chem. Soc., vol. 83, pp. 291-293, Mar. 2006.

Moghaddam et al., "Zirconium(IV) Oxide Chloride and Anhydrous Copper(II) Sulfate Mediated Synthesis of 2-Substituted Benzothiazoles," Heteroatom Chemistry, vol. 17, No. 2, pp. 136-141, 2006.

Yoshino et al., "Synthesis of 5-Fluorosubstituted Benzothiazolybenzylphosphonates," J. Heterocyclic Chem., vol. 26, pp. 1039-1043, Jul.-Aug. 1989.

Chaignon et al., "Purification and identification of a *Bacillus* nitroreductase: Potential use in 3,5-DNBTF biosensoring system," Enzyme and Microbial Technology, vol. 39, pp. 1499-1506, 2006.

Jarrett et al., "A New route to Phenanthridine Derivatives," Journal of the Chemical Society, pp. 3818-3823, Apr. 17, 1957.

Douch, "4-Nitrobenzoic acid reductase of *Ascaris lumbricoides var suum*. Substrate specificity and reaction products," Xenobiotica, vol. 5, No. 7, Jul. 1975.

Angermaier et al., "On nitroaryl reductase activities in several Clostridia," Hoppe Seylers Z Physoil Chem., vol. 364, No. 12, Dec. 1983.

Villanueva, "The Purification of a Nitro-reductase from *Nocardia V*," The Journal of Biological Chemistry, vol. 239, No. 3, pp. 773-776, Mar. 1964.

*Primary Examiner* — Herbert J Lilling
(74) *Attorney, Agent, or Firm* — Oliff & Berridge, PLC

(57) ABSTRACT

The present invention relates to an enzyme substrate for detecting nitroreductase activity of formula (I) below:

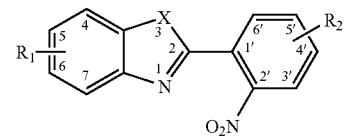

in which X is S, NX1, O or NX1-CO; R1 is nothing or a substituent selected from Cl, $CH_3$, Br, F, I, alkyl, aryl and carboxyl; R2 is nothing or a substituent selected from Cl, O—$CH_2$—O, O—$CH_3$, F, diethylenediamine-$CH_3$, NR3R4, Br, I, alkyl, aryl, carboxyl, $NO_2$ and

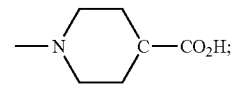

R3 and R4 are independently H or an alkyl group containing from 1 to 4 carbon atoms; and X1 is selected from H, $CH_3$, $C_2H_4Ph$, OH, alkyl and aryl.

13 Claims, No Drawings

NITROREDUCTASE ENZYMATIC SUBSTRATES

The invention relates to novel enzyme substrates for detecting nitroreductase activity. These substrates can be employed in uses comprising a step of enzymatic reduction producing a physicochemical signal, in particular in microbiology, biochemistry, immunology, molecular biology, histology, etc.

A very large number of media currently exist for detecting microorganisms. This detection may be based especially on the use of particular substrates, specific for an enzyme of the microorganism that it is desired to detect. In general, synthetic substrates for enzymes are constituted of a first part specific for the enzymatic activity to be revealed, and of a second part which acts as a label, generally a chromogenic or fluorescent label. Thus, in the case of bacteria, by virtue of the choice of substrates, depending on whether or not there is a reaction, it is possible to characterize the nature of a microorganism. A nitroreductase activity may in particular be used to reveal a group, a genus or a species of bacteria. It may also be used to monitor the reducing metabolism of microorganisms, for example linked to their, growth or to the inhibition of this growth.

The ability of certain bacteria to reduce nitroaromatic compounds has been known for many years. Asnis (1957) reported the isolation of a flavoprotein from E. coli extracts which was capable of reducing p-nitrobenzoic acid. Since this report, nitroaryl reductase activity has been identified in various varieties of organisms. This includes strictly aerobic microorganisms such as Pseudomonas spp. (Won et al. 1974) and Nocardia spp. (Villanueva 1964), strictly anaerobic microorganisms such as Clostridium spp. (Ancermaier & Simon 1983) and Veillonella spp. (McCormick et al. 1976), or else fungi (Masuda & Ozaki 1993) and eukaryotic parasites (Douch 1975). A range of substrates exist which have been denoted as being capable of being reduced by bacterial nitroaryl reductases. They are especially nitroaromatic compounds such as p-nitrobenzoic acid, p-nitrophenol, p-nitroaniline and 2,4,6-trinitrotoluene (McCormick et al. 1976).

In general, the detection of nitroreductase enzymatic activity is carried out by indirect methods such as monitoring the disappearance of the substrate or of a cofactor. For example, Kitamura et al. (1983) have studied the reduction of methyl p-nitrobenzoate and of a range of other nitroaromatic compounds with E. coli extracts. However, this method is not very sensitive and is not suitable for detection in a heterogeneous medium. Mention may also be made of application WO 00/28073 which describes a nitrocoumarin-based fluorogenic substrate for the direct detection of nitroaryl reductase activities. This type of nitroaromatic compound is capable of producing, after reduction, a highly fluorescent compound which is therefore readily detectable. However, this substrate is not very suitable for detection in a heterogeneous medium.

The present invention therefore proposes to improve the nitroreductase substrates for the detection of microorganisms. Compared with the existing substrates, these novel substrates are easy to synthesize and can be used in particular in gel media for detecting microorganisms since they produce a coloration that does not diffuse in the reaction medium.

Before proceeding with the description of the invention, the definitions below are given in order to facilitate the disclosure of the invention.

The term enzyme substrate is intended to mean a substrate that can be modified by an enzyme so as to give a product which allows the direct or indirect detection of a microorganism, of a cell or of an organelle. In the case of nitroreductase substrates, this substrate comprises in particular a nitrate function which is partially or totally reduced by the enzymatic activity to be revealed, the reduction of this nitrate function modifying certain physicochemical properties of the molecule, enabling this reduction to be followed.

The substrates according to the invention are particularly suitable for use in flow cytometry because, since the product of the reduction remains mainly localized in the cell expressing the enzymatic activity, it is possible to specifically count the cells expressing this activity, or even to separate them from the rest of the sample.

The substrates according to the invention are also suitable for use in histoenzymology because, since the product of the reduction remains mainly localized at the site of the reduction, it is possible to specifically identify the cells or organelles expressing this activity within a tissue.

Owing to their low toxicity, the substrates according to the invention are suitable for monitoring cell culture nitroreductase activity.

The substrates according to the invention are also very suitable for use in a detection and/or identification medium since they produce a coloration or a fluorescence that does not diffuse in the reaction medium. In the present application, the term "coloration" is used to cover a coloration in the visible spectrum, which is absorption of light, or a fluorescence, which is absorption at one wavelength ($\lambda_{ex}$) and emission at a higher wavelength ($\lambda_{em}$).

The substrates of the invention may be salified, i.e. in the form of a salt such as a chloride, bromide, potassium or trifluoroacetate salt.

The term nitroreductase is intended to mean an enzyme that can totally or partially reduce an $NO_2$ group.

The term alkyl group is intended to mean a chain of saturated hydrocarbon-based groups, such as, in particular, a $C_1$-$C_6$ alkyl, i.e. a straight or branched alkyl containing from 1 to 6 carbon atoms. By way of example, mention may be made of methyl, ethyl, propyl, isopropyl, butyl, t-butyl, pentyl, isopentyl and hexyl.

The term aryl group is intended to mean a functional group (or substituent) which derives from an aromatic ring, for instance a $C_6$-$C_{10}$ aromatic ring, in particular phenyl, benzyl, 1-naphthyl or 2-naphthyl.

The term carboxyl group is intended to mean in particular a functional group composed of a carbon atom, linked via a double bond to a first oxygen atom, and via a single bond to a second oxygen atom, itself negatively charged or linked to a hydrogen atom. Depending on the $pK_a$ of the molecule and of the pH of the medium, the carboxyl group may be in ionized form, i.e. without H linked to the second oxygen atom, which is then negatively charged.

The term reaction medium is intended to mean a medium comprising all the elements necessary for the expression of a metabolism and/or for the growth of microorganisms, of a cell or of an organelle. This reaction medium can be used in flow cytometry, histoenzymology, cell culture, etc., or as a microorganism detection and/or identification medium.

The reaction medium may be solid, semi-solid or liquid. The term "solid medium" is intended to mean, for example, a gelled medium. Agar is the conventional gelling agent in microbiology for culturing microorganisms, but it is possible to use gelatin or agarose. A certain number of preparations are commercially available, for instance Columbia agar, Trypticase-soy agar, MacConkey agar, Sabouraud agar or, more generally, those described in the Handbook of Microbiological Media (CRC Press). The reaction medium may comprise one or more elements in combination, such as amino acids, peptones, carbohydrates, nucleotides, minerals, vitamins, antibiotics, surfactants, buffers, phosphate salts, ammonium salts, sodium salts or metal salts. The medium may also comprise a colorant. By way of indication, mention may be made, as colorant, of Evans blue, neutral red, sheep blood, horse blood, an opacifier such as titanium oxide, nitroaniline, malachite green, brilliant green, etc.

The reaction medium may be a detection and/or identification medium, i.e. a developing medium or a culture and developing medium. In the first case, the microorganisms are cultured before inoculation, and in the second case, the detection and/or identification medium also constitutes the culture medium.

The term biological sample is intended to mean a clinical sample, derived from a biological fluid specimen, or a food sample, derived from any type of food. This sample may thus be liquid or solid and mention may be made, without limitation, of a clinical sample of blood, plasma, urine or feces, or of specimens from the nose, throat, skin, wounds or cerebrospinal fluid, a food sample from water or from a drink such as milk or a fruit juice; from yogurt, from meat, from eggs, from vegetables, from mayonnaise, from cheese; from fish, etc., or a food sample derived from an animal feed, such as in particular a sample derived from animal meal. The sample may also be a specimen from the clinical environment, a livestock specimen or a specimen from food, cosmetic or pharmaceutical production. The term "environment specimen" is intended to mean in particular a specimen taken from a surface, from a liquid, from a starting material or from a product.

For the purpose of the present invention, the term microorganism covers bacteria, particularly Gram-positive bacteria and Gram-negative bacteria, yeasts, parasites, fungi, and more generally, organisms that are generally single-cell, invisible to the naked eye, and that can be multiplied and manipulated in the laboratory.

By way of Gram-negative bacteria, mention may be made of the bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia, Actinobacillus, Alcaligenes, Bordetella, Cedecea, Erwinia, Pantoea, Ralstonia, Stenotrophomonas, Xanthomonas* and *Legionella*.

By way of Gram-positive bacteria, mention may be made of the bacteria of the following genera: *Aerococcus, Enterococcus, Streptococcus, Staphylococcus, Bacillus, Lactobacillus, Listeria, Clostridium, Gardnerella, Kocuria, Lactococcus, Leuconostoc, Micrococcus, Falkamia, Gemella, Pediococcus, Mycobacterium* and *Corynebacterium*. By way of yeasts, mention may be made of the yeasts of the following genera: *Candida, Cryptococcus, Saccharomyces* and *Trichosporon*.

In this respect, the invention relates to an enzyme substrate for detecting nitroreductase activity, of formula (I) below:

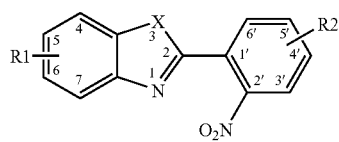

in which:
X is S, NX1, O or NX1—CO;
R1 is nothing or a substituent selected from Cl, $CH_3$, Br, F, I, alkyl, aryl and carboxyl;

R2 is nothing or a substituent chosen from Cl, O—$CH_2$—O, O—$CH_3$, F, diethylenediamine-$CH_3$, NR3R4, Br, I, alkyl, aryl, carboxyl, $NO_2$ and

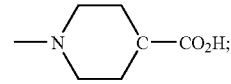

R3 and R4 are independently H or an alkyl group containing from 1 to 4 carbon atoms;
X1 is selected from H, $CH_3$, $C_2H_4Ph$, OH, alkyl and aryl.

The bond between the nitrogen in the 1-position and the carbon in the 2-position on the heterocycle may be single (1,2-dihydro) or double, preferably double.

Of course, the substrate according to the invention may comprise several substituents, i.e. several groups R1, R2 in various positions on the ring. When R2 is O—$CH_2$—O, R2 is a ring fused to the nitrophenol, two of their ring members being shared. When R1 and/or R2 is an alkyl or aryl group, it may also be substituted with one or more substituents such as OH, carboxyl, Br, Cl, F or I.

When X is NX1-CO, the ring comprising X is preferably a 6-membered ring, comprising NX1 in the 3-position and a C linked via a double bond to an O in the 4-position of said 6-membered ring.

According to one preferred embodiment of the invention, X is S.

According to another preferred embodiment of the invention, X is NX1.

According to another preferred embodiment of the invention, X is O.

According to another preferred embodiment of the invention, X is NX1-CO.

According to one preferred embodiment of the invention, R1 is in the 5-position.

According to one preferred embodiment of the invention, R2 is in the 4'-position.

According to another preferred embodiment of the invention, R2 is in the 5'-position.

According to another preferred embodiment of the invention, R2 is in the 4'-position and in the 5'-position.

According to one particular embodiment of the invention, said enzyme substrate corresponds to the formula (I) above, in which:
X is O:
R1 and R2 are nothing.

According to one particular embodiment of the invention, said enzyme substrate corresponds to the formula (I) above, in which:
X is O;
R1 is Cl, preferably in the 5-position;
R2 is nothing.

According to one particular embodiment of the invention, said enzyme substrate corresponds to the formula (I) above, in which:
X is O;
R1 is $CH_3$, preferably in the 5-position;
R2 is nothing.

According to one particular embodiment of the invention, said enzyme substrate corresponds to the formula (I) above, in which:
X is O;
R1 is nothing;
R2 is Cl, preferably in the 5'-position.

According to one particular embodiment of the invention, said enzyme substrate corresponds to the formula (I) above, in which:
X is O;
R1 is nothing;
R2 is O—CH$_2$—O, preferably fused to the nitrophenol in the 4'- and 5'-position.

According to one particular embodiment of the invention, said enzyme substrate corresponds to the formula (I) above, in which:
X is O;
R1 is nothing;
R2 is O—CH$_3$, preferably in the 4'- and 5'-position.

According to one particular embodiment of the invention, said enzyme substrate corresponds to the formula (I) above, in which:
X is O;
R1 is nothing;
R2 is F, preferably in the 5'-position.

According to one particular embodiment of the invention, said enzyme substrate corresponds to the formula (I) above, in which:
X is O;
R1 is nothing;
R2 is diethylenediamine-CH$_3$, preferably in the 5'-position.

According to one particular embodiment of the invention, said enzyme substrate corresponds to the formula (I) above, in which:
X is NX1;
X1 is CH$_3$, preferably in the 3-position;
R1 is nothing;
R2 is nothing.

According to one particular embodiment of the invention, said enzyme substrate corresponds to the formula (I) above, in which:
X is NX1;
X1 is CH$_3$;
R1 is nothing;
R2 is Cl, preferably in the 5'-position.

According to one particular embodiment of the invention, said enzyme substrate corresponds to the formula (I) above, in which:
X is NX1;
X1 is CH$_3$;
R1 is nothing;
R2 is O—CH$_2$—O, preferably fused to the nitrophenol in the 4'- and 5'-position.

According to one particular embodiment of the invention, said enzyme substrate corresponds to the formula (I) above, in which:
X is NX1;
X1 is C$_2$H$_4$Ph;
R1 is nothing;
R2 is nothing.

According to one particular embodiment of the invention, said enzyme substrate corresponds to the formula (I) above, in which:
X is NX1;
X1 is C$_2$H$_4$Ph;
R1 is nothing;
R2 is Cl, preferably in the 5'-position.

According to one particular embodiment of the invention, said enzyme substrate corresponds to the formula (I) above, in which:
X is NX1;
X1 is C$_2$H$_4$Ph;
R1 is nothing;
R2 is O—CH$_2$—O, preferably fused to the nitrophenol in the 4'- and 5'-position.

According to one particular embodiment of the invention, said enzyme substrate corresponds to the formula (I) above, in which:
X is S;
R1 is nothing;
R2 is F, preferably in the 5'-position.

According to one particular embodiment of the invention, said enzyme substrate corresponds to the formula (I) above, in which:
X is NX1-CO;
X1 is H;
R1 and R2 are nothing.

According to one particular embodiment of the invention, said enzyme substrate corresponds to the formula (I) above, in which:
X is NX1-CO;
X1 is CH$_3$;
R1 and R2 are nothing.

According to one particular embodiment of the invention, said enzyme substrate corresponds to the formula (I) above, in which:
X is NX1-CO;
X1 is CH$_3$;
R1 is nothing;
R2 is Cl, preferably in the 5'-position.

According to one particular embodiment of the invention, said enzyme substrate corresponds to the formula (I) above, in which:
X is NX1;
X1 is H;
R1 and R2 are nothing.

According to one particular embodiment of the invention, said enzyme substrate corresponds to the formula (I) above, in which:
X is NX1-CO;
X1 is H;
R1 is nothing;
R2 is Cl in the 5'-position.

According to one particular embodiment of the invention, said enzyme substrate corresponds to the formula (I) above, in which:
X is S;
R1 is nothing;
R2 is diethylenediamine-CH$_3$, preferably in the 5'-position.

According to one particular embodiment of the invention, said enzyme substrate corresponds to the formula (I) above, in which:
X is S;
R1 is nothing;
R2 is

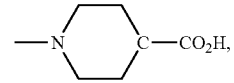

preferably in the 5'-position.

According to one particular embodiment of the invention, said enzyme substrate corresponds to the formula (I) above, in which:
X is O;
R1 is nothing;
R2 is NO$_2$, preferably in the 4'-position.

According to one particular embodiment of the invention, said enzyme substrate corresponds to the formula (I) above, in which:
X is S;
R1 is nothing;
R2 is nothing.

According to one particular embodiment of the invention, said enzyme substrate corresponds to the formula (I) above, in which:
X is S;
R1 is nothing;
R2 is F, preferably in the 5'-position;
the bond between the nitrogen in the 1-position and the carbon in the 2-position in the heterocycle is single (1,2-dihydro).

Preferably, the substrate according to the invention is selected from the substrates described in table 1.

TABLE 1

Examples of substrates according to the invention

| Substrates | Reference | X | X1 | R1 | R2 |
|---|---|---|---|---|---|
| 2-(2'-Nitrophenyl)benzoxazole | Substrate 1 64 | O | — | — | — |
| 2-(2'-Nitrophenyl)-5-chlorobenzoxazole | Substrate 2 VLS259, 72 | O | — | Cl | — |
| 2-(2'-Nitrophenyl)-5-methylbenzoxazole | Substrate 3 VLS271, 75 | O | — | $CH_3$ | — |
| 2-(2'-Nitro-5'-chlorophenyl)benzoxazole | Substrate 4 VLS269, 71 | O | — | — | Cl |
| 2-(2'-Nitro-4',5'-methylenedioxyphenyl)benzoxazole | Substrate 5 70 | O | — | — | O—$CH_2$—O |
| 2-(2'-Nitro-4',5'-dimethoxyphenyl)benzoxazole | Substrate 6 VLS261, 73 | O | — | — | O—$CH_3$, O—$CH_3$ |
| 2-(2'-Nitro-5'-fluorophenyl)benzoxazole | Substrate 7 OF20B | O | — | — | F |
| 2-(2'-Nitro-5'-(N-methylpiperazinyl)phenyl)benzoxazole | Substrate 8 OF29A | O | — | — | Diethylenediamine-$CH_3$ |
| 2-(2'-Nitrophenyl)-3-methylbenzimidazole | Substrate 9 40 | NX1 | $CH_3$ | — | — |
| 2-(2'-Nitro-5'-chlorophenyl)-3-methylbenzimidazole | Substrate 10 44 | NX1 | $CH_3$ | — | Cl |
| 2-(2'-Nitro-4'-5'-methylenedioxyphenyl)-3-methylbenzimidazole | Substrate 11 45 | NX1 | $CH_3$ | — | O—$CH_2$—O |
| 2-(2'-Nitrophenyl)-3-phenethylbenzimidazole | Substrate 12 54 | NX1 | $C_2H_4Ph$ | — | — |
| 2-(2'-Nitro-5'-chlorophenyl)-3-phenethylbenzimidazole | Substrate 13 61 | NX1 | $C_2H_4Ph$ | — | Cl |
| 2-(2'-Nitro-4'-5'-methylenedioxyphenyl)-3-phenethylbenzimidazole | Substrate 14 62 | NX1 | $C_2H_4Ph$ | — | O—$CH_2$—O |
| 2-(2'-Nitro-5'-fluorophenyl)benzothiazole | Substrate 15 OF26A | S | — | — | F |
| 2-(2'-Nitrophenyl)quinoxazol-4-one | Substrate 16 | NX1-CO | H | — | — |
| 2-(2'-Nitrophenyl)-3-methylquinoxazol-4-one | Substrate 17 | NX1-CO | $CH_3$ | — | — |
| 2-(2'-Nitro-5'-chlorophenyl)-3-methyl-quinoxazol-4-one | Substrate 18 | NX1-CO | $CH_3$ | — | Cl |
| 2-(2'-Nitrophenyl)benzimidazole | Substrate 19 | NX1 | H | — | — |
| 2-(2'-Nitro-5'-chlorophenyl)quinoxazol-4-one | Substrate 20 | NX1-CO | H | — | Cl |
| 2-(2'-Nitro-5'-chlorophenyl)benzothiazole | Substrate 21 CVX-16 | S | — | — | Cl |
| 2-(2'-Nitrophenyl)benzothiazole | Substrate 22 | S | — | — | — |
| 2-(2'-Nitro-5'-(N-methylpiperazinyl)phenyl)benzo-thiazole | Substrate 23 | S | — | — | Diethylenediamine-$CH_3$ |
| 2-(2'-Nitro-5'-N-(carboxylpiperidinyl)phenyl)benzo-thiazole | Substrate 24 | S | — | — | 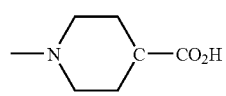 |
| 2-(2',4'-Dinitrophenyl)benzoxazole | Substrate 25 OF91C | O | — | — | $NO_2$ |
| 2-(2'-Nitrophenyl)-1,2-dihydrobenzothiazole | Substrate 26 | S | — | — | — |
| 2-(2'-Nitro-5'-fluorophenyl)-1,2-dihydrobenzothiazole | Substrate 27 | S | — | — | F |

The invention also relates to a reaction medium comprising at least one enzyme substrate as defined above.

The invention also relates to a microorganism detection and/or identification medium comprising at least one enzyme substrate as defined above. Preferably, said substrate is at a concentration of between 1 and 1000 mg/l, preferably between 10 and 500 mg/l. According to one particular embodiment of the invention, said medium also comprises at least one other enzyme substrate, specific for an enzymatic activity different to that detected by the substrate according to the invention.

The enzymatic hydrolysis of the other substrate(s) generates a detectable signal, different to the signal detected by the substrate of the invention, for instance different colored or fluorescent products, so as to allow the demonstration, such as the detection and/or the identification and/or the quantification, of one or more microorganisms. By way of other specific substrate, use may be made of any other substrate conventionally used in the detection of microorganisms. The concentration of the other specific enzyme substrate is generally between 0.01 and 1 g/l. Those skilled in the art will be able to readily determine such a concentration according to the substrate used. By way of indication, it is possible to combine the substrates according to the invention with peptidase, osidase, esterase or reductase enzyme substrates. In particular, it is possible to combine a substrate according to the invention with an osidase substrate, such as 5-bromo-4-chloro-3-indolyl-β-glucoside, or alizarin-β-galactoside, or with an esterase substrate, such as 5-bromo-6-chloro-3-indoxyl octanoate or 5-bromo-3-indoxyl phosphate.

According to one particular embodiment of the invention, said medium also comprises at least one other enzyme substrate specific for the enzymatic activity detected by the substrate according to the invention.

Through the particular choice of substrates, it is then possible to identify groups of microorganisms expressing the same enzymatic activity. The concentration of the other specific enzyme substrate is generally between 0.01 and 1 g/l. Those skilled in the art will be able to readily determine such a concentration according to the substrate used. In particular, it is possible to combine a substrate according to the invention with a fluorogenic substrate based on nitrocoumarin as described in application WO 00/28073.

The invention also relates to the use of the enzyme substrates as defined above or of a detection and/or identification medium as defined above, for detecting at least one nitroreductase activity in microorganisms.

The invention also relates to a method for detecting at least one nitroreductase activity in microorganisms, characterized in that it comprises or is constituted of the following steps:
  a) providing a detection and/or identification medium as defined above,
  b) inoculating the medium with a biological sample to be tested,
  c) leaving this to incubate, and
  d) revealing the presence of at least one nitroreductase activity.

The inoculation of the microorganisms can be carried out by any of the inoculation techniques known to those skilled in the art. An incubation step may be carried out at a temperature for which the expression of the enzymatic activity that it is desired to detect is optimal, and which those skilled in the art can readily select according to the enzymatic activity and the microorganisms to be detected. Step d) may be carried out by visual examination, by colorimetry or fluorimetry. During step d), the presence of the nitroreductase activity can be revealed alone or in combination with other enzymatic activities.

The examples below are given by way of explanation and are in no way limiting in nature. They will make it possible to understand the invention more clearly.

EXAMPLES

1—Synthesis of Substrates

X is S

Substrate 22: 2-(2'-Nitrophenyl)benzothiazole

A mixture of 1 eq of 2-aminophenol, of ethanol and of 1 eq of 2-nitrobenzaldehyde was refluxed, using an oil bath, at a temperature of 110° C. for one hour.

The mixture was cooled to ambient temperature and the precipitate was covered by filtration. In order to recover a maximum amount of product, the round-bottomed flask was rinsed with the filtrate so as to recover a significant portion by evaporation.

The solid was dried in a desiccator under reduced pressure so as to obtain the intermediate product.

The solid obtained above was dissolved in 100 ml of dichloromethane, and then 1 eq of 2,3-dicyano-5,6-dichloro-para-benzoquinone was added in small portions at ambient temperature. The reaction was carried out overnight, and after filtration, the glassware was rinsed with DCM in order to recover the maximum amount of product since it is soluble in DCM.

The solvent was evaporated off under reduced pressure in order to obtain the product.

Substrate 15: 2-(2'-Nitro-5'-fluorophenyl)benzothiazole

A mixture of 3.00 g (0.024 mol) of 2-aminothiophenol and 4.05 g (0.024 mol) of 5-nitro-3-fluorobenzaldehyde in ethanol (150 ml) was refluxed for 2 hours. After having been cooled to ambient temperature, the solution was concentrated under reduced pressure. The remaining solid was diluted in a mixture of water and ethyl acetate (500 ml), and the aqueous phase was extracted a further two times using ethyl acetate (2×50 ml). The combined organic phases were dried ($MgSO_4$), filtered and concentrated so as to obtain the crude product, which was recrystallized from ethanol.

A mass of 1.28 g of fine red crystals of OF54A2 was obtained with a yield of 47% and a measured melting point of 156-158° C.

The data which were obtained by NMR are indicated below:
$^1$H NMR (270 MHz, $CDCl_3$): δ=6.87 (1H, t, J=4 Hz, Ar—H), 6.89 (1H, s, Ar—H), 7.05 (1H, t, J=4 Hz, Ar—H), 7.11 (1H, d, J=3 Hz, Ar—H), 7.13 (1H, d, J=3 Hz, Ar—H), 7.69 (1H, dd, J=9 Hz, Ar—H), 8.17 (1H, dd, J=9 Hz, Ar—H).

Substrate 23: 2-(2'-Nitro-5'-(N-methylpiperazinyl)phenyl)benzothiazole (OF80A)

0.31 g (0.0030 mol) of N-methylpiperazine was added to the mixture of 0.41 g (0.015 mol) of 2-(2'-nitro-5'-fluorophenyl)benzothiazole and 0.32 g (0.0023 mol) of $K_2CO_3$ in 5 ml of dimethyl sulfoxide. The reaction was stirred magnetically and heated at 90° C., the progression thereof being verified by TLC.

After the reaction was complete (at least 8 hours), the reaction mixture was diluted in ethyl acetate (77 ml), and the organic phase thus obtained was carefully washed with 2×65 ml of water, then with 65 ml of brine, and dried using sodium sulfate so as to obtain 0.36 g of a highly electrostatic orangey-yellow solid, OF80A, with a yield of 68%. Purification by column chromatography can be carried out if necessary; this was not the case for us.

$^1$H NMR (270 MHz, CDCl$_3$): δ=2.35 (3H, s, CH$_3$), 2.45 (2H, t, J=7 Hz, CH$_2$—CH$_2$), 3.49 (2H, t, J=7 Hz, CH$_2$—CH$_2$), 6.85 (1H, d, J=7 Hz, Ar—H), 6.90 (1H, t, J=7 Hz, Ar—H), 7.41 (1H, d, J=7 Hz, Ar—H), 7.43 (1H, d, J=7 Hz, Ar—H), 7.85 (1H, d, J=7 Hz, Ar—H), 8.05 (1H, t, J=7 Hz, Ar—H). LC-MS-DI m/z Found: 355.57 (C$_{18}$H$_{18}$N$_4$O$_2$S) (M+H): requires M. 354.43.

Substrate 21: 2-(2'-Nitro-5'-chlorophenyl)benzothiazole

Substrate No. 21 was synthesized in a manner analogous to the synthesis of 2-(2'-nitro-5'-fluorophenyl)benzothiazole (substrate No. 15).

X is O

Substrate 1-2-(2'-Nitrophenyl)benzoxazole

A mixture of 8.73 g (0.0800 mol) of 2-aminophenol, of 20 ml of ethanol and of 12.09 g (0.0800 mol) of 2-nitrobenzaldehyde was refluxed, using an oil bath, at a temperature of 110° C. for one hour.

The mixture was cooled to ambient temperature and the precipitate was recovered by filtration. In order to recover a maximum amount of product, the round-bottomed flask was rinsed with the filtrate so as to obtain a significant portion by evaporation.

The solid was dried in a desiccator under reduced pressure so as to obtain 13.25 g of 2-(2'-nitrobenzylidineamino)phenol with a yield of 69%.

The solid obtained above was dissolved in 100 ml of dichloromethane, and then 12.43 g (0.0547 mol) of 2,3-dicyano-5,6-dichloro-para-benzoquinone were added in small portions at ambient temperature. The reaction was carried out overnight. After filtration, the glassware was rinsed with DCM in order to recover the maximum amount of product since it is soluble in DCM.

The solvent was evaporated off under reduced pressure so as to obtain 8.39 g of 2-(2-nitrophenyl)benzoxazole, a beigy-brown solid, with a yield of 64%.

The data which were obtained by NMR are indicated below:

$^1$H NMR (270 MHz, CDCl$_3$): δ=7.40 (1H, t, J=5 Hz, Ar—H), 7.42 (1H, t, 1=5 Hz, Ar—H), 7.50 (1H, d, J=7 Hz, Ar—H), 7.72 (1H, t, J=5 Hz, Ar—H), 7.73 (1H, t, J=5 Hz, Ar—H), 7.80 (1H, d, J=7 Hz, Ar—H), 7.89 (1H, d, J=7 Hz, Ar—H), 8.15 (1H, d, J=7 Hz, Ar—H).

Substrate 2-2-(2'-Nitrophenyl)-5-chlorobenzoxazole—VLS259

Substrate No. 2 was synthesized in a manner analogous to the synthesis of 2-(2'-nitrophenyl)benzoxazole (substrate No. 1).

Substrate 6-2-(2'-Nitro-4',5'-dimethoxyphenyl)benzoxazole-VLS261

1. Synthesis of 2-((3'-chloro-6'-nitrobenzylidene)amino)phenol (VLS 263)

A mixture of 2.18 g (0.02 mol) of 2-hydroxyaniline and 3.73 g (0.02 mol) of 2-nitro-5-chlorobenzaldehyde in ethanol was refluxed for 3-4 hours. The resulting crystalline precipitate was collected and dried in a desiccator at reduced pressure. A mass of 1.98 g of fine orange crystals was obtained with a yield of 80% and a measured melting point of 144-146° C.

The data which were obtained by NMR are indicated below:

$^1$H-NMR: (CDCl$_3$) δ 6.95 (1H, t, J=8 Hz, Ph-H), 7.05 (1H, dd, J=8 Hz, J=1.2 Hz, Ph-H), 7.10 (1H, s (broad), OH), 7.28 (1H, t, J=8 Hz, Ph-H), 7.33 (1H, dd, J=8 Hz, J=1.4 Hz, Ph-H), 7.60 (1H, dd, J=8.66 Hz, J=2.2 Hz, 4'H), 8.05 (1H, d, J=8.66 Hz, 5'H), 8.23 (1H, d, J=2.4 Hz, 2'H), 9.27 (1H, s, =CH—) ν$_{max}$, cm$^{-1}$ 3442 (OH), 1558 (NO$_2$), 1376 (NO$_2$), 1521 (C=N), 1341 (OH), 1301 (OH), 1143 (C—N), 1176 (C—O), 1461 (Ar—H), 756 (C—Cl).

2. Synthesis of 2-(2'-nitro-5'-chlorophenyl)benzoxazole (VLS269)

1.14 g (0.005 mol) of 2,3-dichloro-5,6-dicyano-1,4-benzoquinone (DDQ) were added, over a period of 5 minutes, to 2-((3'-chloro-6'-nitrobenzylidene)amino)phenol stirred in dichloromethane at ambient temperature. The mixture was left to stir for 2 days, filtered and evaporated so as to obtain the product. A mass of 0.97 g of a greeny-brown powder was obtained with a yield of 70% and a measured melting point of 130-132° C.

The data which were obtained by NMR are indicated below:

High-resolution M.S.E.I for C$_{13}$H$_7$ClN$_2$O$_3$ Calculated mass of molecular ion 274.0140 (M+H)$^+$ Measured mass: 274.0141. $^1$H-NMR: (CDCl$_3$) δ 7.40-7.45 (2H, m, Ph-H), 7.56-7.61 (1H, m, Ph-H), 7.65 (1H, dd, J=8.66 Hz, J=2.23 Hz, 4'H), 7.80-7.85 (1H, m, Ph-H), 7.87 (1H, d, J=8.66 Hz, 5'H), 8.16 (1H, d, J=2.23 Hz, 2'H). ν$_{max}$ cm$^{-1}$ 1534 (NO$_2$), 1371 (NO$_2$), 1572 (C=N), 1616 (C=N), 1182 (C—O), 1236 (C—O), 1153 (C—N), 1461 (Ar—H), 743 (C—Cl).

3. Synthesis of 2-(3',4'-dimethoxy-6'-benzylidene)amino)phenol (VLS 260)

A mixture of 3.27 g (0.03 mol) of 2-hydroxyaniline and 6.33 g (0.03 mol) of 6-nitroveratraldehyde in ethanol was refluxed for 3-4 hours. The resulting crystalline precipitate was collected and dried in a desiccator at reduced pressure. A mass of 8.20 g of fine orange crystals was obtained with a yield of 90% and a measured melting point of 196-198° C.

The data which were obtained by NMR are indicated below:

$^1$H-NMR: (CDCl$_3$) δ. $^1$H-NMR: (CDCl$_3$) δ 4.00 (3H, s, CH$_3$O), 6.92 (1H, t, J=7 Hz, Ph-H), 7.01 (1H, dd, J=7 Hz, J=1.4 Hz, Ph-H), 7.12 (1H, s (broad), OH), 7.22 (1H, t, J=7 Hz, Ph-H), 7.32 (1H, dd, J=7 Hz, J=1.4 Hz, Ph-H), 7.62 (1H, s, 5'H), 7.69 (1H, s, 3'H), 9.25 (1H, s, =CH—). ν$_{max}$ cm$^{-1}$ 3416 (OH), 1566 (NO$_2$), 1384 (NO$_2$), 1589 (C=N), 1344 (OH), 1317 (OH), 1181 (C—N), 1149 (C—O), 1461 (Ar—H), 2838 (OMe).

4. Synthesis of 2-(2'-nitro-4',5'-dimethoxyphenyl)benzoxazole (VLS 261)

2.27 g (0.01 mol) of 2,3-dichloro-5,6-dicyano-1,4-benzoquinone (DDQ) were added, over a period of 5 minutes, to 3.04 g (0.01 mol) of 2-(3',4'-dimethoxy-6'-benzylidene)amino)phenol stirred in dichloromethane at ambient temperature. The mixture was left to stir for 2 days, filtered and evaporated so as to obtain the product. A mass of 2.76 g of an orangey-brown powder was obtained with a yield of 90% and a measured melting point of 148-146° C.

The data which were obtained by NMR are indicated below:

High-resolution M.S.E.I for $C_{15}H_{12}N_2O_5$ Calculated mass of molecular ion 301.0819 (M+H)$^+$Measured mass: 301.0819. $^1$H-NMR: (CDCl$_3$) δ 4.00 (6H, d, J=2.7 Hz, (OCH$_3$)$_2$), 7.37-7.41 (2H, m, Ph-H), 7.43 (1H, s, 5'H), 7.52 (1H, s, 2'H), 7.53-7.57 (1H, m, Ph-H), 7.78-7.82 (1H, m, Ph-H). $\nu_{max}$ cm$^{-1}$ 1519 (NO$_2$), 1378 (NO$_2$), 1582 (C=N), 1189 (C—N), 1177 (C—O), 1448 (Ar—H), 2850 (OMe).

Substrate 7-2-(2'-Nitro-5'-fluorophenyl)benzoxazole —OF20B

A mixture of 10.91 g (0.100 mol) of 2-aminophenol, of 200 ml of ethanol and of 16.91 g (0.100 mol) of 2-nitro-5-fluorobenzaldehyde was refluxed, using an oil bath, at a temperature of 110° C. for one hour.

The mixture was cooled to ambient temperature and the precipitate was recovered by filtration. In order to recover a maximum amount of product, the round-bottomed flask was rinsed with the filtrate so as to obtain a significant amount by evaporation.

The solid was dried in a desiccator under reduced pressure so as to obtain 24.09 g of OF20A with a yield of 93%.

The solid obtained above was dissolved in 100 ml of dichloromethane, and then 21.04 g (0.0927 mol) of 2,3-dicyano-5,6-dichloro-para-benzoquinone were added in small portions at ambient temperature. The reaction was carried out overnight, and after filtration, the glassware was rinsed with DCM so as to recover the maximum amount of product since it is soluble in DCM.

The solvent was evaporated off under reduced pressure so as to obtain 14.49 g of OF20B, a beigy-brown solid, with a yield of 61%.

The data which were obtained by NMR are indicated below:

$^1$H NMR (270 MHz, CDCl$_3$): δ=7.37 (1H, d, J=3 Hz, Ar—H), 7.43 (1H, t, J=5 Hz, Ar—H), 7.45 (1H, s, Ar—H), 7.59 (1H, t, J=5 Hz, Ar—H), 7.82 (1H, d, J=3 Hz, Ar—H), 7.85 (1H, d, J=3 Hz, Ar—H), 7.96 (1H, dd, J=9 Hz, Ar—H), 8.15 (1H, d, J=7 Hz, Ar—H).

Substrate 3: 2-(2'-Nitrophenyl)-5-methylbenzoxazole

Substrate No. 3 was synthesized in a manner analogous to the synthesis of 2-(2'-nitrophenyl)benzoxazole (substrate No. 1).

Substrate 4: 2-(2'-Nitro-5'-chlorophenyl)benzoxazole

Substrate No. 4 was synthesized in a manner analogous to the synthesis of 2-(2'-nitrophenyl)benzoxazole (substrate No. 1).

Substrate 5: 2-(2'-Nitro-4',5'-dimethylenedioxyphenyl)benzoxazole

Substrate No. 5 was synthesized in a manner analogous to the synthesis of 2-(2'-nitrophenyl)benzoxazole (substrate No 1).

Substrate 8: 2-(2'-Nitro-5'-(N-methylpiperazinyl)phenyl)benzoxazole (OF29A)

1.01 g (0.010 mol) of N-methylpiperazine were added to the mixture of 1.29 g (0.005 mol) of 2-(2'-nitro-5'-fluorophenyl)benzoxazole and 1.04 g (0.0075 mol) of K$_2$CO$_3$ in 9 ml of dimethyl sulfoxide. The reaction was stirred magnetically and heated at 90° C., the progression thereof being verified by TLC.

Once the reaction was complete (at least 8 hours) the reaction mixture was diluted in ethyl acetate (77 ml), and the organic phase thus obtained was carefully washed with 2×65 ml of water, then with 65 ml of brine, and dried using sodium sulfate so as to obtain 1.23 g of yellow/golden petals of OF29A with a yield of 73%. Purification by column chromatography may be carried out if necessary; this was not the case for us.

$^1$H NMR (270 MHz, CDCl$_3$): δ=2.35 (3H, s, CH$_3$), 2.57 (2H, t, J=7 Hz, CH$_2$—CH), 3.48 (2H, t, J=7 Hz, CH$_2$—CH), 6.95 (1H, d, J=7 Hz, Ar—H), 6.98 (1H, d, J=7 Hz, Ar—H), 7.21 (1H, d, J=7 Hz, Ar—H), 7.28 (1H, s, Ar—H), 7.39 (1H, t, J=9 Hz, Ar—H), 7.41 (1H, t, J=7 Hz, Ar—H), 7.55 (1H, t, J=7 Hz, Ar—H), 7.61 (1H, t, J=7 Hz, Ar—H), 8.1 (1H, d, J=7 Hz, Ar—H).

m.p.: 122-126

LC-MS-DI m/z Found: 339.54 (C$_{18}$H$_{18}$N$_4$O$_3$) (M+H): requires M. 338.37.

X is NX1-CO

Substrate 20—2-(2'-Nitro-5'-chlorophenyl)quinoxazol-4-one

1. Synthesis of 1,2-dihydro-2-(2'-nitro-5'-chlorophenyl)quinoxazolin-4-one (VLS 276)

A mass of 2.31 g (0.017 mol) of 2-aminobenzamide and 3.14 g (0.017 mol) of 3-chloro-6-nitrobenzaldehyde was refluxed in ethanol for 1 hour. The mixture was then cooled, and the orange crystals obtained were harvested and dried in a desiccator at reduced pressure. A mass of 3.97 g of light orange crystals was obtained with a yield of 76% and a measured melting point of 234-236° C.

The data which were obtained by NMR are indicated below:

$^1$H-NMR: (DMSO) δ 6.35 (1H, t, J=2 Hz, CH), 6.70 (1H, d, J=1 Hz, Ph-H (8H)), 6.80 (1H, t, J=7 Hz, Ph-H (6H)), 7.05 (1H, s (broad), NH), 7.25 (1H, t, J=7 Hz, Ph-H (7H)), 7.65 (1H, d, d, J=6 Hz, J=1.5 Hz, Ph-H (5H)), 7.75 (1H, d, d, J=9 Hz, J=3 Hz, Ph-H (4'H)), 7.85 (1H, d, J=3 Hz, Ph-H (6'H)), 8.15 (1H, d, J=9 Hz, Ph-H (3'H)), 8.30 (1H, d (broad), NH—CO), High-resolution M.S.E.I for C$_{14}$H$_{10}$ClN$_3$O$_3$ Calculated mass of molecular ion 304.0483 (M+H)$^+$. Measured mass: 304.0482 $\nu_{max}$ cm$^{-1}$ 1661 (C=ONH), 1564 (NO$_2$), 1358 (NO$_2$), 1602 (C=N), 774 (C—Cl).

2. Oxidation of 2-(2'-nitro-5'-chlorophenyl)quinoxazolin-4-one (VLS 278)

A mass of 9.10 g (0.03 mol) of 2-(2'-nitro-5'-chlorophenyl)quinoxazolin-4-one was dissolved in 40 ml of anhydrous acetone and was treated with 4.74 g (0.03 mol) of a solution of potassium permanganate in anhydrous acetone. This solution was added dropwise to the mixture over a period of 2-3 hours at ambient temperature. The reaction was then stirred overnight. The excess KMnO$_4$ was eliminated by adding an excess of solid sodium bisulfite. The solution was then filtered and evaporated. A mass of 2.26 g of a pale white powder was obtained with a yield of 25% and a measured melting point of 276-278° C.

The data which were obtained by NMR are indicated below:

High-resolution M.S.E.I for $C_{14}H_8ClN_3O_3$ Calculated mass of molecular ion 302.0327 $(M+H)^+$. Measured mass: 304.0327 $^1$H-NMR: (DMSO) δ 7.55 (1H, t, J=7 Hz, Ph-H (7H)), 7.65 (1H, d, J=8 Hz, Ph-H (4'H)), 7.85 (1H, t, J=7 Hz, Ph-H (6H)), 7.90 (1H, d, d, J=8 Hz, J=2 Hz, Ph-H (5H)), 8.05 (1H, d, J=2 Hz, Ph-H (6'H)), 8.25 (1H, d, J=8 Hz, Ph-H (3'H)). $v_{max}$ cm$^{-1}$ 3132 (NH$_2$), 3070 (NH$_2$), 1578 (NO$_2$), 1368 (NO$_2$), 1603 (NH), 1660 (CONH), 1531 (C=N), 772 (C—Cl).

Substrate 17—2-(2'-Nitrophenyl)-3-methylquinoxazol-4-one

1. Synthesis of 2-amino-N-methylbenzamide (VLS 291)

25 ml of 40% methylamine were added, in small portions, with stirring, while controlling the release of CO$_2$, to 16.20 g (0.099 mol) of isotoic anhydride. The mixture was kept at ambient temperature for 1 hour. The mixture was then neutralized with a 2M solution of HCl, filtered under reduced pressure with a Buchi apparatus, washed several times with water and dried using a desiccator at reduced pressure. A mass of 11.61 g of a gray powder was obtained with a yield of 78%.

2. Synthesis of 2-(2'-nitro-5'-chlorophenyl)-3-methylquinoxazolin-4-one (VLS 292)

A mass of 7.5 g (0.05 mol) of 2-amino-N-methylbenzamide and 9.30 g (0.05 mol) of 3-chloro-6-nitrobenzaldehyde were stirred magnetically and brought to reflux for 2-3 hours. The orange crystals thus obtained were filtered under reduced pressure with a Buchi apparatus and dried using a desiccator at reduced pressure. A mass of 10.38 g of needle-fine orange crystals was obtained with a yield of 66%.

3. Oxidation of VLS 292 (VLS 295b)

A mass of 3.17 g (0.01 mol) of VLS 292b was dissolved in anhydrous acetone. 6.32 g (0.04 mol) of KMnO$_4$ were dissolved in anhydrous acetone and added dropwise to the preceding mixture over a period of 1 to 2 hours. The reaction was then left to stir overnight. Next, the mixture was neutralized with sodium metabisulfite, filtered and evaporated so as to remove the excess acetone. A mass of 2.60 g of a white powder was obtained with a yield of 80%.

X is NX1

Substrate 14-2-(2'-Nitro-4',5'-cyclomethylenedioxyphenyl)-3-phenethylbenzimidazole (or 2-(2'-nitro-4',5'-methylenedioxyphenyl)-3-phenethylbenzimidazole)

1. N-Phenylethyl-2-nitroaniline (VLS 209)

A mass of 4.8 g (0.04 mol) of 2-phenylethylamine was added dropwise, at ambient temperature, to a mixture of 5.6 g (0.04 mol) of 2-fluoronitrobenzene and 11.06 g (0.08 mol) of anhydrous potassium carbonate in 30 ml of DMSO. The mixture was heated at 100° C. for 3 hours. The mixture was then cooled to ambient temperature and was added to 100 ml of water, which resulted in the precipitation of a light orange compound. The solid was recovered by filtration and dried using a desiccator at reduced pressure. A mass of 9.4 g of orange crystals was obtained with a yield of 98%. The melting point found was coherent with the theoretical value, i.e. 64-66° C.

The data which were obtained by NMR are indicated below:

$^1$H-NMR: (CDCl$_3$) δ 3.00 (2H, t, J=7 Hz, —CH$_2$—), δ 3.55 (2H, t, J=7 Hz, —Cl$_2$—), δ 6.65 (1H, m, Ph-H), δ 6.85 (1H, dd, J=8 Hz, J=2 Hz, Ph-H), δ 7.20-7.50 (6H, m, Ph-H), δ 8.10 (1H, s(broad), NH), δ 8.20 (1H, dd, J=8 Hz, J=2 Hz, Ph-H).

2. N-Phenylethyl-1,2-diaminobenzene (VLS 210)

A solution of 0.38 g (0.01 mol) of sodium borohydride was added to a suspension of 0.52 g (0.002 mol) of copper acetylacetonate in ethanol, with magnetic stirring under nitrogen at ambient temperature. 2.42 g (0.01 mol) of the nitro compound of VLS 209 in ethanol were added to this solution, followed by 0.76 g (0.02 mol) of sodium borohydride in ethanol. The mixture was left to stir overnight under nitrogen at ambient temperature. The mixture was then concentrated in order to remove the excess ethanol, and water was added. An extraction was then carried out with 2×20 ml of DCM and the organic phase was washed several times with water, dried using potassium carbonate and concentrated on a rotary evaporator. A mass of 1.69 g of a dark oily liquid, which subsequently solidified, was obtained, with a yield of 80%. The melting point found was coherent with the theoretical value, i.e. 42-44° C.

The data which were obtained by NMR are indicated below:

$^1$H-NMR: (CDCl$_3$) δ 2.95 (2H, t, J=7 Hz, —CH$_2$—), δ 3.27 (2H, s (broad), NH$_2$), δ 3.38 (2H, t, J=7 Hz, —CH$_2$), δ 6.69 (3H, m, Ph-H), δ 6.82 (1H, m, Ph-H), δ 7.10-7.40 (5H, m, Ph-H).

3. 2-(2'-Nitro-4',5'-cyclomethylenedioxyphenyl)-3-phenethylbenzimidazole (VLS 213) (or 2-(2'-nitro-4',5'-methylenedioxyphenyl)-3-phenethylbenzimidazole)

8.60 g (0.014 mol) of oxone (potassium monopersulfate) were added, over a period of 15 minutes at ambient temperature, to a solution, stirred magnetically, of 5.08 g (0.024 mol) of N-phenylethyl-1,2-diaminobenzene, of 4.8 g (0.024 mol) of 6-nitropiperonal in 25 ml of DMF and of 1 ml of water. The mixture was cooled with a bath of water since the reaction was exothermic, and left to stir overnight. Water was then added to the mixture and two consecutive extractions with DCM were carried out. The combined organic phases were washed with water several times, dried (MgSO$_4$) and concentrated so as to give the yellow/brown-colored crude product. Recrystallization with ethanol was carried out in order to purify the compound. A mass of 6.19 g of brown crystals was obtained with a yield of 67% and a measured melting point of 162-164° C.

The data which were obtained by NMR are indicated below:

High-resolution M.S.E.I for $C_{22}H_{17}N_3O_4$ Calculated mass of molecular ion 388.1292 (M+H)$^+$. Measured mass: 388.1297.'H-NMR: (CDCl$_3$) δ 3.10 (2H, t, J=7 Hz, —CH$_2$—), δ 4.20 (2H, t, J=7 Hz, —CH$_2$—), δ 6.02 (1H, s, Ph-H), δ 6.18 (2H, s, O—CH$_2$—O), δ 6.80 (2H, dd, J=8 Hz, J=2 Hz, Ph-H), δ 7.10-7.40 (5H, m, Ph-H), δ 7.48 (1H, m, Ph-H), δ 7.65 (1H, s, Ph-H), δ 7.80 (1H, m, Ph-H). $v_{max}$ cm$^{-1}$ 1364 (NO$_2$), 1523 (NO$_2$), 1610 (C=N), 1152 (C—N), 1207 (C—N), 1089 (C—O), 1473 (C—H), 728 (—CH$_2$).

Substrate 12-2-(2'-Nitrophenyl)-3-phenethylbenzimidazole-54

Substrate No. 12 was synthesized in a manner analogous to the synthesis of 2-(2'-nitro-4',5'-cyclomethylenedioxyphenyl)-3-phenethylbenzimidazole (substrate No. 14).

2—Use of substrates according to the invention (substrates Nos. 1; 2; 3; 4; 5; 6; 7; 8; 15; 12; 21; 23) for detecting nitroreductase activity a) Preparation of the Medium A mass of 40 mg of each substrate was dissolved in 4 ml of dimethylformamide (DMF). This solution was entirely taken up in 400 ml of Columbia agar autoclaved beforehand and kept molten at 50° C. The final concentration for each substrate was 100 mg/l.

Each of the media was distributed into Petri dishes 90 mm in diameter, in a proportion of 20 ml per dish.

b) Inoculation and Incubation 18 microorganism strains derived from collections and belonging to various species of bacteria and of yeasts were inoculated onto these media by semi-quantitative isolation of 10 µl of a suspension at 0.5 McFarland diluted to 1/20. The media were incubated for 24 hours at 37° C., then the colonies formed were examined visually under UV illumination at 360-365 nm.

c) Reading of Results

The results obtained are given in tables 2 to 5.

TABLE 2

Intensity and color of the fluorescence produced by various microorganism strains in the presence of substrates according to the invention

| | Substrate according to the invention | | | | |
|---|---|---|---|---|---|
| | No. 2 2-(2'-Nitrophenyl)-5-chlorobenzoxazole | No. 6 2-(2'-Nitro-4',5'-dimethoxyphenyl)benzoxazole | No. 7 2-(2'-Nitro-5'-fluorophenyl)benzoxazole | No. 15 2-(2'-Nitro-5'-fluorophenyl)benzothiazole | No. 12 2-(2'-Nitrophenyl)-3-phenethylbenzimidazole |
| *Escherichia coli* NCTC 10418 | +[1] Blue | + Blue | ++ Blue | ++ Blue | − |
| *Serratia marcescens* NCTC 10211 | + Blue | + Blue | ++ Blue | ++ Blue | − |
| *Pseudomonas aeruginosa* NCTC 10662 | − | − | − | − | − |
| *Acinetobacter baumanii* ATCC 19606 | +/− Blue | − | + Blue | + Blue | − |
| *Yersinia enterocolitica* NCTC 11176 | +/− Blue | − | − | − | − |
| *Salmonella typhimurium* NCTC 74 | − | − | ++ Blue | ++ Blue | − |
| *Enterobacter cloacae* NCTC 11936 | + Blue | + Blue | ++ Blue | ++ Blue | − |
| *Morganella morganii* 462403 | +/− Blue | +/− Blue | ++ Blue | ++ Blue | +/− Blue |
| *Bacillus subtilis* NCTC 9372 | − | − | − | − | − |
| *Enterococcus faecalis* NCTC 775 | − | − | − | − | − |
| *Enterococcus faecium* NCTC 11047 | − | − | − | − | − |
| *Staphylococcus epidermidis* NCTC 11047 | − | − | − | − | − |
| *Staphylococcus aureus* NCTC 6571 | + Blue | + Blue | ++ Blue | ++ Blue | − |
| *Staphylococcus aureus* NCTC 11939 | + Blue | + Blue | ++ Blue | ++ Blue | − |
| *Streptococcus pyogenes* NCTC 8306 | − | − | − | − | − |
| *Listeria monocytogenes* NCTC 11994 | − | − | − | − | − |
| *Candida albicans* ATCC 90028 | − | − | − | − | − |
| *Candida glabrata* NCPF3943 | − | − | − | − | − |

[1]intensity of fluorescence, − = no fluorescence detected, +/− = weak fluorescence, + = medium fluorescence, ++ = strong fluorescence

TABLE 3

Growth, color and fluorescence produced by various microorganism strains in the presence of substrates according to the invention

|  | Substrate 1 | | Substrate 5 | |
|---|---|---|---|---|
|  | G | F | G | F |
| *Escherichia coli* NCTC 10418 | + | ++ violet | + | ++ violet |
| *Serratia marcescens* NCTC 10211 | + | ++ violet | + | ++ violet |
| *Pseudomonas aeruginosa* NCTC 10662 | + | ++ violet | + | + violet |
| *Burkholderia cepacia* 1222 | + | ++ violet | + | + violet |
| *Yersinia enterocolitica* NCTC 11176 | + | ++ violet | + | − |
| *Salmonella typhimurium* NCTC 74 | + | ++ violet | ++ | ++ violet |
| *Citrobacter freundii* 46262 (wild) | + | ++ violet | + | ++ violet |
| *Morganella morganii* 462403 (wild) | + | ++ violet | + | ++ violet |
| *Enterobacter cloacae* NCTC 11936 | + | ++ violet | + | ++ violet |
| *Providencia rettgeri* NCTC 7475 | + | ++ violet | + | + violet |
| *Bacillus subtilis* NCTC 9372 | + | − | + | − |
| *Enterococcus faecails* NCTC 775 | + | ++ violet | + | − |
| *Enterococcus faecium* NCTC 7171 | + | + violet | + | − |
| *Staphylococcus epidermidis* NCTC 11047 | + | + violet | + | − |
| *Staphylococcus aureus* NCTC 6571 | + | ++ violet | + | ++ violet |
| MRSA NCTC 11939 | + | ++ violet | + | ++ violet |
| *Streptococcus pyogenes* NCTC 8306 | + | + violet | + | − |
| *Listeria monocyto genes* NCTC 11994 | + | ++ violet | + | + violet |
| *Candida albicans* ATCC 90028 | +/− | − | + | − |
| *Candida glabrata* NCPF 3943 | No G | − | +/− | − |

G: growth
F: fluorescence

TABLE 4

Intensity and color of the fluorescence produced by various microorganism strains in the presence of substrates according to the invention

|  | Substrate 15 | Substrate 23 |
|---|---|---|
| *Escherichia coli* NCTC 10418 | ++ turquoise | − |
| *Serratia marcescens* NCTC 10211 | ++ turquoise | + green |
| *Pseudomonas aeruginosa* NCTC 10662 | + turquoise | + yellow |
| *Acinetobacter baumanii* ATCC 19606 | + turquoise | − |
| *Yersinia enterocolitica* NCTC 11176 | − | − |
| *Salmonella typhimurium* NCTC 74 | ++ turquoise | + yellow |
| *Citrobacter freundii* 46262 (wild) | ++ turquoise | + yellow |
| *Morganella morganii* 462403 (wild) | ++ turquoise | + yellow |
| *Enterobacter cloacae* NCTC 11936 | ++ turquoise | + yellow |
| *Providencia rettgeri* NCTC 7475 | ++ turquoise | + yellow |
| *Bacillus subtilis* NCTC 9372 | − | − |
| *Enterococcus faecails* NCTC 775 | − | − |
| *Enterococcus faecium* NCTC 7171 | − | − |
| *Staphylococcus epidermidis* NCTC 11047 | − | − |
| *Staphylococcus aureus* NCTC 6571 | ++ turquoise | V. yellow |
| MRSA NCTC 11939 | ++ turquoise | +/− yellow |
| *Streptococcus pyogenes* NCTC 8306 | − | − |
| *Listeria monocytogenes* NCTC 11994 | − | − |
| *Candida albicans* ATCC 90028 | − | − |
| *Candida glabrata* NCPF 3943 | − | − |

1: fluorescence intensity,
− = no fluorescence detected,
+/− = weak fluorescence,
+ = medium fluorescence,
++ = strong fluorescence

TABLE 5

Detection of various strains of *S. aureus* in the presence of substrates according to the invention

|  | Substrate 2 | | Substrate 3 | | Substrate 4 | | Substrate 6 | | Substrate 7 | | Substrate 8 | | Substrate 21 | | Substrate 15 | |
|---|---|---|---|---|---|---|---|---|---|---|---|---|---|---|---|---|
|  | 24 h No. of strains detected | 48 h No. of strains detected | 24 h No. of strains detected | 48 h No. of strains detected | 24 h No. of strains detected | 48 h No. of strains detected | 24 h No. of strains detected | 48 h No. of strains detected | 24 h No. of strains detected | 48 h No. of strains detected | 24 h No. of strains detected | 48 h No. of strains detected | 24 h No. of strains detected | 48 h No. of strains detected | 24 h No. of strains detected | 48 h No. of strains detected |
| *S. aureus* (including MRSA) 10 strains | 10 | 10 | 10 | 10 | 10 | 10 | 10 | 10 | 10 | 10 | 10 | 10 | 10 | 10 | 10 | 10 |
| *S. epidermidis* 2 strains | 0 | 2 | 0 | 2 | 0 | 2 | 0 | 2 | 0 | 2 | 0 | 2 | 0 | 2 | 0 | 2 |
| *Staph* spp 12 strains | 12 | 12 | 12 | 12 | 12 | 12 | 12 | 12 | 12 | 12 | 12 | 12 | 12 | 12 | 12 | 12 |
| *Enterococcus* 6 strains | 0 | 1 | 0 | 1 | 0 | 1 | 0 | 1 | 0 | 1 | 0 | 1 | 0 | 1 | 0 | 1 |

Contrary to what is observed with substrates based on 7-nitrocoumarin (AMC), such as 7-nitrocoumarin-3-carboxylic acid, for all the substrates according to the invention that were tested, the fluorescence was localized at the colony only, or in the immediate vicinity.

These results show that substrates Nos. 2, 3, 4, 6, 7, 8, 15 and 21 make it possible to distinguish or identify the *Staphylococcus aureus* strains, in particular the MRSA (methicillin-resistant *Staphylococcus aureus*) strains, from most of the other Gram-positive bacterial strains. Owing to the medical importance of this species, this may be very useful for the rapid and specific detection of *S. aureus* in clinical specimens, but also in food specimens.

Moreover, depending on the substituents on the aromatic rings, the specificity of the substrates according to the invention with respect to Gram-negative bacteria is variable. By way of example, substrates 2, 7 and 15 make it possible to distinguish *Pseudomonas aeruginosa* from *Acinetobacter baumanii*; *Salmonella typhimurium* are strongly positive with substrates 7 and 15 and negative with substrates 2, 6 and 12. Substrate 12 is specific for *Morganella morganii*.

d) Conclusion

The substrates according to the invention make it possible to use many reaction media for microbiology. These media are very useful for detecting, counting and/or identifying microorganisms of medical, industrial or environmental interest.

The invention claimed is:
1. A microorganism detection and/or identification medium for microorganisms having at least one nitroreductase activity comprising at least one enzyme substrate for detecting a nitroreductase activity of formula (I) below:

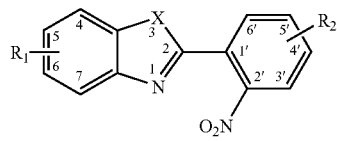

in which:
X is S, NX1, O or NX1-CO;
R1 is nothing or a substituent selected from Cl, CH₃, Br, F, I, alkyl, aryl and carboxyl;
R2 is nothing or a substituent selected from Cl, O—CH₂—O, O—CH₃, F, diethylenediamine-CH₃, NR3R4, Br, I, alkyl, aryl, carboxyl, NO₂ and

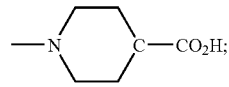

R3 and R4 are independently H or an alkyl group containing from 1 to 4 carbon atoms; and
X1 is selected from H, CH₃, C₂H₄Ph, OH, alkyl and aryl.
2. A method for detecting at least one nitroreductase activity in microorganisms, the method comprising:
a) inoculating, with a biological sample to be tested, a medium comprising at least one substrate of formula (I) below:

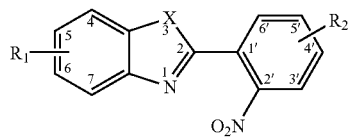

in which:
X is S, NX1, O or NX1-CO;
R1 is nothing or a substituent selected from Cl, CH₃, Br, F, I, alkyl, aryl and carboxyl;

R2 is nothing or a substituent selected from Cl, O—CH₂—O, O—CH₃, F, diethylenediamine-CH₃, NR3R4, Br, I, alkyl, aryl, carboxyl, NO₂ and

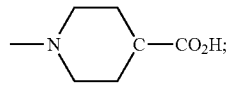

R3 and R4 are independently H or an alkyl group containing from 1 to 4 carbon atoms; and
X1 is selected from H, CH₃, C₂H₄Ph, OH, alkyl and aryl,
b) leaving the biological sample to incubate, and
c) revealing the presence of at least one nitroreductase activity when present.
3. The medium of claim 1, in which:
X is O;
R1 is Cl; and
R2 is nothing.
4. The medium of claim 1, in which:
X is O;
R1 is CH₃; and
R2 is nothing.
5. The medium of claim 1, in which:
X is O;
R1 is nothing; and
R2 is Cl.
6. The medium of claim 1, in which:
X is O;
R1 is nothing; and
R2 is O—CH₃.
7. The medium of claim 1, in which:
X is O;
R1 is nothing; and
R2 is F.
8. The medium of claim 1, in which:
X is O;
R1 is nothing; and
R2 is diethylenediamine-CH₃.
9. The medium of claim 1, in which:
X is NX1;
X1 is CH₃;
R1 is nothing; and
R2 is nothing.
10. The medium of claim 1, in which:
X is NX1;
X1 is CH₃;
R1 is nothing; and
R2 is Cl.
11. The medium of claim 1, in which:
X is NX1;
X1 is CH₃;
R1 is nothing; and
R2 is O—CH₂—O.
12. The medium of claim 1, in which:
X is NX1;
X1 is C₂H₄Ph;
R1 is nothing; and
R2 is nothing.
13. The medium of claim 1, in which:
X is S;
R1 is nothing; and
R2 is F.

* * * * *